United States Patent [19]

Kieturakis

[11] Patent Number: 5,569,183
[45] Date of Patent: Oct. 29, 1996

[54] METHOD FOR PERFORMING SURGERY AROUND A VIEWING SPACE IN THE INTERIOR OF THE BODY

[75] Inventor: Maciej J. Kieturakis, San Carlos, Calif.

[73] Assignee: Archimedes Surgical, Inc., Menlo Park, Calif.

[21] Appl. No.: 255,273

[22] Filed: Jun. 1, 1994

[51] Int. Cl.[6] .................................................. A61M 31/00
[52] U.S. Cl. ............................................. 604/51; 606/185
[58] Field of Search ................................... 604/164, 192, 604/264, 53, 160, 165, 167, 170–171, 274, 51; 606/185, 191

[56] References Cited

U.S. PATENT DOCUMENTS

| | | |
|---|---|---|
| 4,191,191 | 3/1980 | Auburn . |
| 4,535,773 | 8/1985 | Yoon . |
| 4,601,710 | 7/1986 | Moll . |
| 4,654,030 | 3/1987 | Moll et al. . |
| 4,763,662 | 8/1988 | Yokoi . |
| 4,770,163 | 9/1988 | Ono et al. . |
| 4,836,205 | 6/1989 | Barrett . |
| 4,881,537 | 11/1989 | Henning . |
| 5,041,089 | 8/1991 | Mueller et al. . |
| 5,116,353 | 5/1992 | Green . |
| 5,147,316 | 9/1992 | Castillenti . |
| 5,147,376 | 9/1992 | Pianetti . |
| 5,203,773 | 4/1993 | Green . |
| 5,209,736 | 5/1993 | Stephens et al. . |
| 5,224,952 | 7/1993 | Deniega et al. . |
| 5,226,890 | 7/1993 | Ianniruberto et al. . |
| 5,232,451 | 8/1993 | Freitas et al. . |
| 5,258,003 | 11/1993 | Ciaglia . |
| 5,271,380 | 12/1993 | Riek et al. . |
| 5,279,567 | 1/1994 | Ciaglia et al. . |
| 5,312,357 | 5/1994 | Buijs et al. . |
| 5,334,185 | 8/1994 | Giesy et al. . |
| 5,336,237 | 8/1994 | Chin et al. . |
| 5,336,252 | 8/1994 | Cohen . |
| 5,348,541 | 9/1994 | Lyell . |
| 5,395,030 | 3/1995 | Kuramoto et al. . |

Primary Examiner—Randall L. Green
Assistant Examiner—Perry E. Van Over
Attorney, Agent, or Firm—Skjerven, Morrill, MacPherson, Franklin & Friel; Norman R. Klivans

[57] ABSTRACT

A surgical dissector and method for facilitating fiberoptic viewing when developing a minimally invasive accessway to a surgical objective in the interior of the body. The dissector or guide is used to dissect tissues along an anatomic plane under direct fiberoptic vision. A balloon is provided to further dissect and retract tissue along the dissected accessway to provide an adequate depth of field for fiberoptic viewing through transparent walls of the balloon. The dissection allows a surgeon safely to make additional incisions into the region of the fiberoptic viewing space and to perform surgical procedures under fiberoptic vision by manipulating an accessory instrument on the exterior surface of the inflated balloon that is disposed within the dissected space.

10 Claims, 6 Drawing Sheets

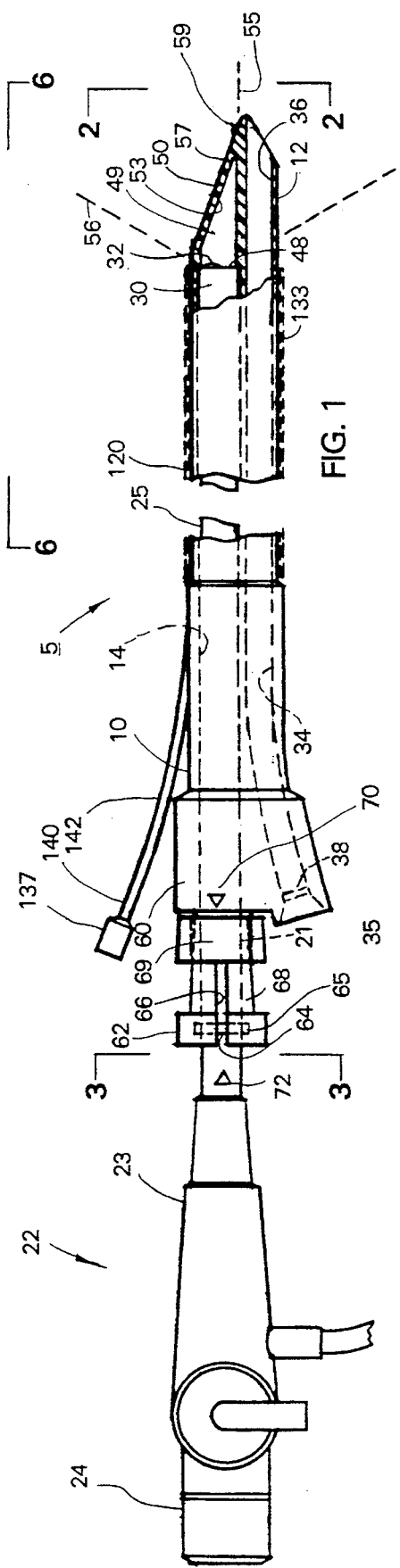
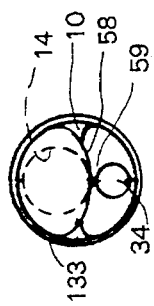
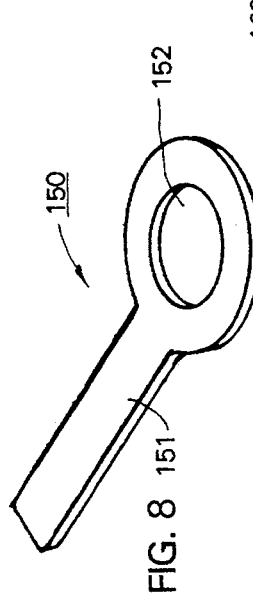
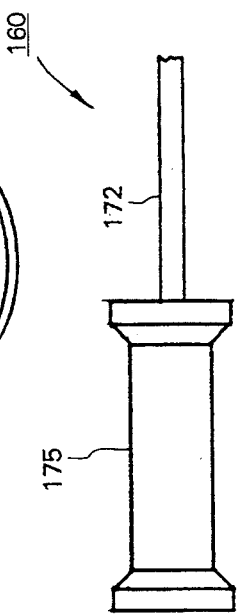

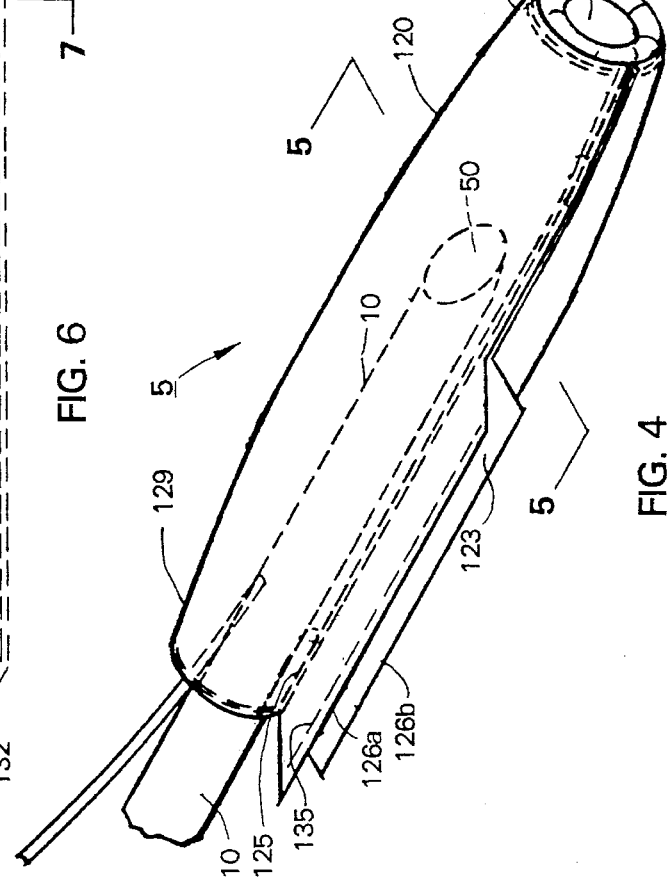

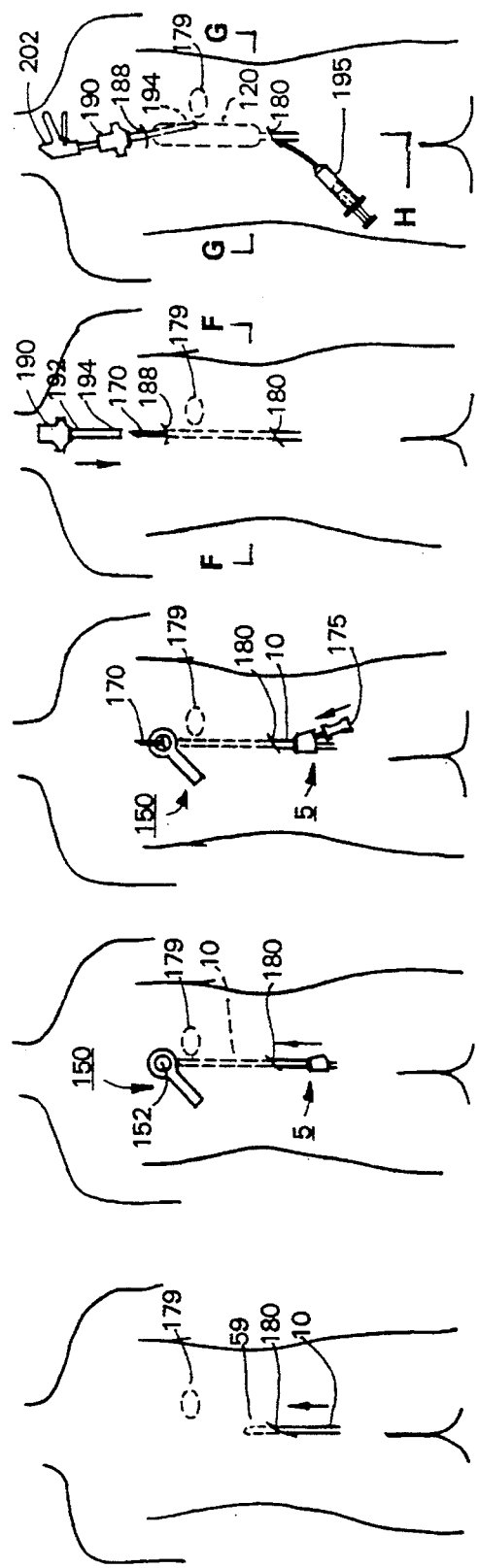

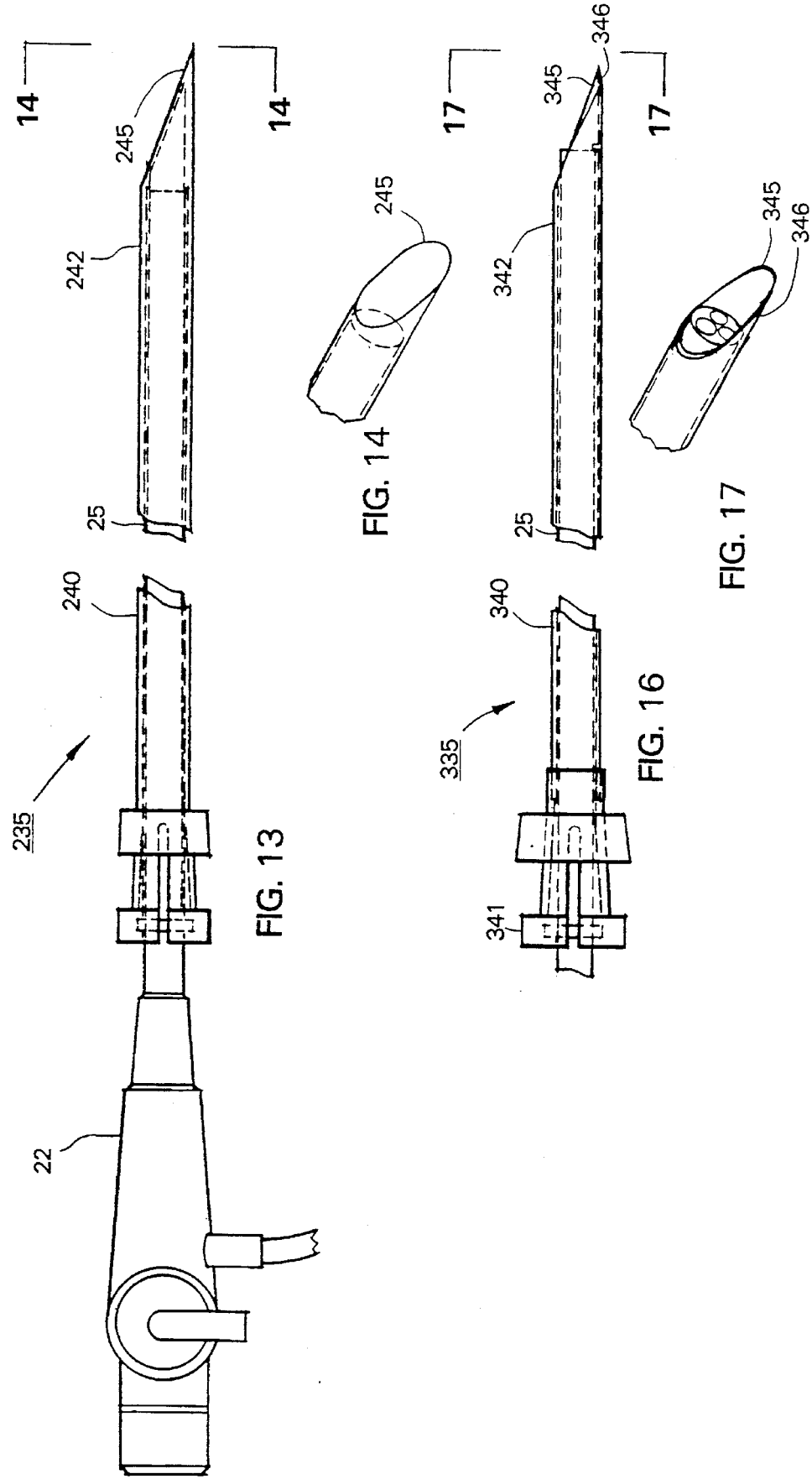

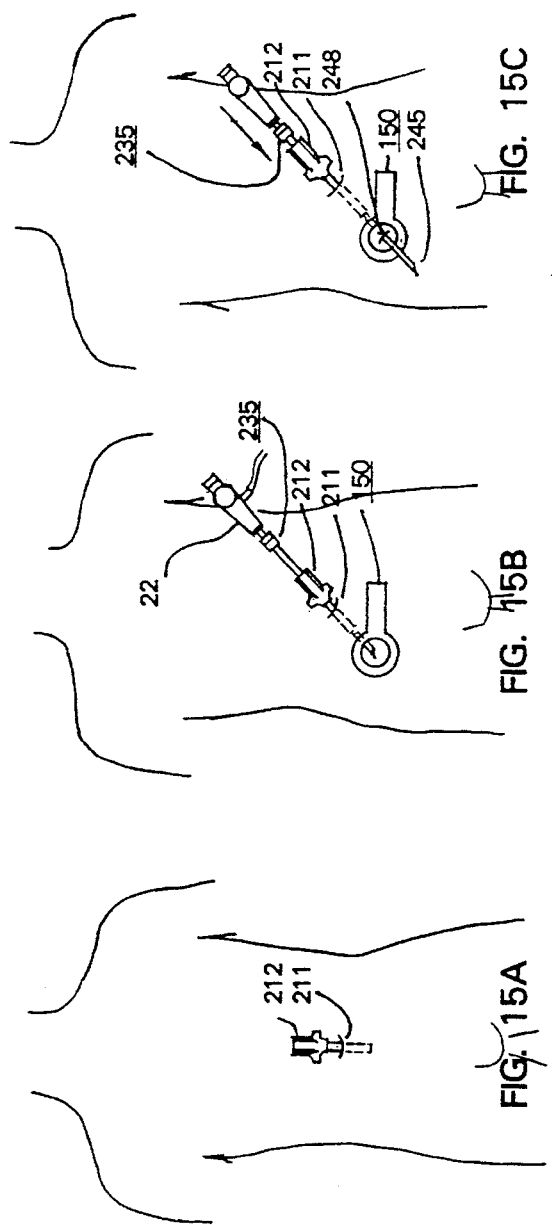
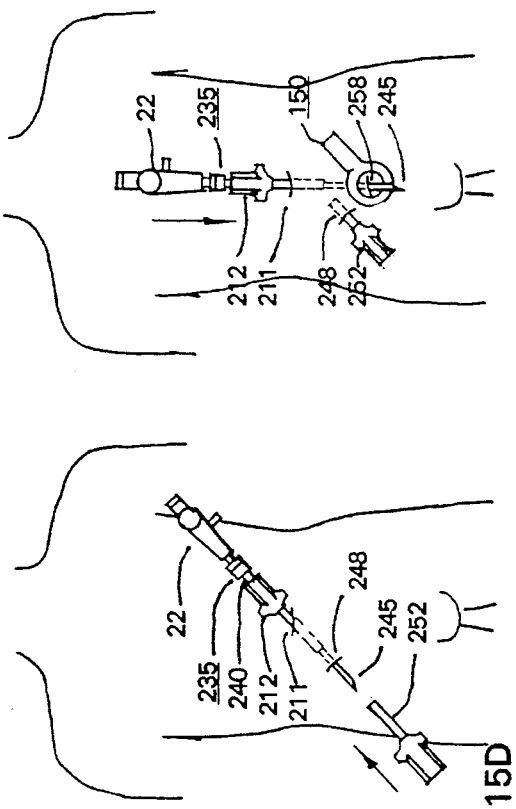

METHOD FOR PERFORMING SURGERY AROUND A VIEWING SPACE IN THE INTERIOR OF THE BODY

BACKGROUND OF THE INVENTION

1. Field of the Invention

This invention relates to a surgical instrument and method for developing a "minimally invasive" accessway to a surgical objective in the interior of the body by dissecting tissues along planes of lower resistance. The invention further relates to dissection and retraction of tissue to provide an adequate depth of field for fiberoptic viewing.

2. Description of the Prior Art

Surgeons in the past have used blunt-tipped instruments as well as balloons in connection with endoscopic surgery to dissect tissue in order to develop a working space in the interior of the body. Typically, the development of such a working space is done blindly or under endoscopic viewing only if at least one accessory port or accessway is established. To perform a surgery in such a working space, the working space is maintained by insufflation with carbon dioxide gas which provides room for viewing with an endoscope as well as room for manipulating accessory instruments. To introduce such accessory instruments into the working space, additional incisions typically are made by plunging a sharp-tipped trocar through the distended body wall overlying the insufflated working space.

It has been found that it may be undesirable to dissect accessways and anatomic spaces blindly. It also has been found that it may be difficult to make additional incisions into a dissected anatomic space particularly if of limited volume or if overlying delicate anatomic structures. It also has been found that insufflation of a working space with carbon dioxide causes tissue emphysema which may be undesirable for particular patients because of excessive carbon dioxide absorption into the blood, thus making a "minimally invasive" endoscopic approach unsuitable.

An illustrative example of a procedure that cannot be performed endoscopically under conventional practice is the division of a nerve along the spinal column. An open surgical approach to the division of such a nerve also is undesirable because it is time consuming and results in excessive postoperative pain and recovery time as well as resulting in a disfiguring six inch incision along the patient's spine. There is therefore a need for new instruments and methods for developing a "minimally invasive" accessway to the interior of the body and for performing a surgery under direct fiberoptic vision within the interior of the body, and particularly for accomplishing an endoscopic division of a nerve along the spinal column.

SUMMARY OF THE INVENTION

In general, the instrument of the present invention dissects an accessway through tissue in a body from a first region to a second region and further dissects and retracts the anatomic space along the accessway and in the second region with a balloon. The instrument includes a transparent tipped dissector-guide having an interior lumen (cavity) dimensioned to accommodate a viewing scope together with a working channel for an elongate trocar. The dissector-guide affords the surgeon contemporaneous vision through the distal (far) end of the cylindrically shaped guide as it traverses the interior of the body. The inflatable balloon has transparent walls and is disposed in a "hot dog bun" shape around the guide.

In an exemplary method, the surgeon wishes to divide a dorsal ramus nerve to alleviate back pain in the patient's right side that is lateral to the fifth thoracic vertebrae. The surgeon makes a small incision in the midline of the patient's back somewhat below the fifth thoracic vertebrae. The surgeon advances the tip of the guide through the incision then pushes the blunt tip inwardly and then upwardly to the right of the spinous process while contemporaneously viewing the advancement of the tip through the endoscope thus dissecting an accessway. After advancing the tip somewhat above the fifth thoracic vertebrae, the surgeon introduces an elongate semi-rigid "inside-out" trocar through the working channel and endoscopically views the interior of the body wall to select a desirable location for an additional incision. The surgeon then pushes the tip of the "inside-out" trocar outwardly until the tip protrudes outwardly from the skin thus making an additional incision. A cannula assembly is inserted over the "inside-out" trocar tip and into the incision. Thereafter, the surgeon inflates the elongate balloon that surrounds the guide to dissect a larger anatomic or viewing space along the guide. The surgeon may move the guide longitudinally within the still inflated balloon to view nerves that "tent" inwardly into the transparent balloon walls. Thereafter, the surgeon introduces an accessory dividing instrument (e.g., scissors) through the cannula and advances the instrument along the interface between the exterior of the balloon and the surrounding tissue and under direct fiberoptic vision he may divide one or more nerves.

In general, the present invention provides an instrument and method for accessing a surgical objective that lies within tissue of the body by advancing a blunt-tipped guide member from a first region to a second remote region that follows along a line of least resistance in tissue at any given location. The present invention also provides an instrument and method for accessing a surgical objective by advancing a blunt-tipped guide member from a first region to a second remote region that follows along a natural anatomic plane between tissues. The present invention also provides an instrument and method that incorporates fiberoptic viewing to permit contemporaneous vision through the device as the device traverses from the first region to the second region.

The present invention also provides an instrument and method for dissecting and developing a dissected viewing space within the interior of the body to provide adequate depth of field for endoscopic viewing by using an inflatable balloon that dissects tissue by generally applying forces perpendicular to tissue being dissected. The present invention also provides an instrument and method for accomplishing a surgical procedure in the region of a dissected anatomic plane without insufflation of the space with carbon dioxide by utilizing an accessory instrument that is introduced between the exterior wall of the balloon and the surrounding tissue. The invention also provides a method and apparatus incorporated into the guide for making additional incisions between the endoscopic viewing space and the outside of the body, and provides endoscopic viewing from inside of a trocar.

The present invention also provides an instrument and method of the above character in which the guide accommodates an inside-out trocar that has a cross-sectional shape (usually cylindrical) that matches and telescopically cooperates with a cannula that can be inserted over the guide member and into the additional incision from outside the body. The present invention also provides an instrument and method of the above character in which the guide member has a cross-sectional shape (usually cylindrical) that matches and telescopically cooperates with a cannula and the guide can be advanced outwardly through the skin from inside the body.

Additional advantages and features of the present invention appear in the following description in which several embodiments are set forth.

DESCRIPTION OF THE DRAWINGS

FIG. 1 is a side elevational view of a dissector-guide incorporating the present invention with an endoscope disposed therein.

FIG. 2 is an elevational view of the guide shown in FIG. 1 taken along line 2—2 of FIG. 1.

FIG. 3 is a transverse sectional view of the endoscope shown in FIG. 1 taken along line 3—3 of FIG. 1.

FIG. 4 is an isometric view of a portion of the guide of FIG. 1.

FIG. 5 is a sectional view of a portion of the guide of FIG. 4 taken along line 5—5 of FIG. 4.

FIG. 6 is a partial sectional view with a not-to-scale schematic illustration of a portion of the guide of FIG. 1 taken along line 6—6 of FIG. 1.

FIG. 7 is a partial sectional view with a not-to-scale schematic illustration of a portion of the guide of FIG. 1 taken along line 7—7 of FIG. 6.

FIG. 8 is an isometric view of a hold down device of the present invention.

FIG. 9 is a side elevational view of a flexible trocar with a portion of the guide of FIG. 1 in phantom view.

FIG. 10 is a side elevational view of a portion of an alternative flexible trocar.

FIGS. 11A–11E are views of a patient's back showing the manner in which the guide of the present invention is utilized for a nerve division procedure in the patient's back.

FIGS. 11F–11H are sectional views of a patient's back taken respectively along lines F—F, G—G and H—H of FIGS. 11D and 11E.

FIG. 13 is a side elevational view of an alternative embodiment of a guide incorporating the present invention with an endoscope disposed therein.

FIG. 14 is an isometric view of a portion of the guide of FIG. 13 taken along line 14—14 of FIG. 13.

FIGS. 15A–15E are views of a patient's abdomen showing the manner in which the guide of FIG. 13 is utilized for a making in making additional incisions.

FIG. 16 is a side elevational view of an alternative embodiment of a guide incorporating the present invention with an endoscope disposed therein.

FIG. 17 is an isometric view of a portion of the guide of FIG. 16 taken along line 17—17 of FIG. 16.

DETAILED DESCRIPTION OF THE INVENTION

Figures 12A, 12B, 12C, 12D:
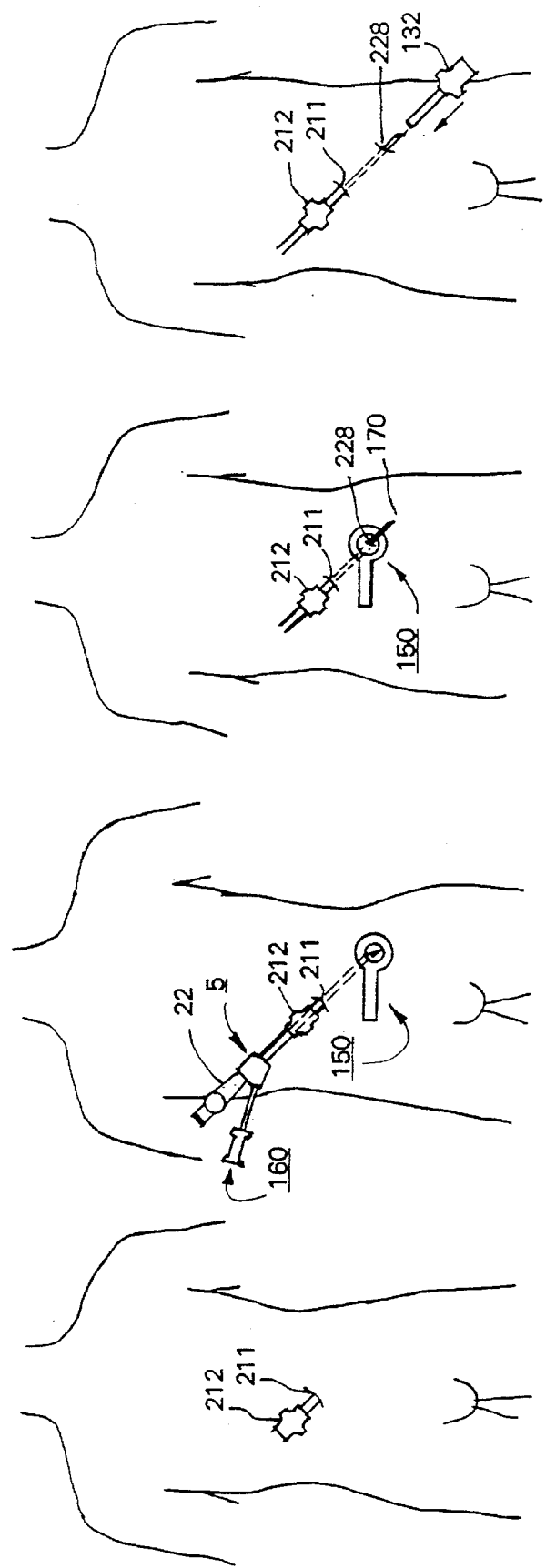
FIGS. 12A–12D are views of a patient's abdomen showing the manner in which the guide of the present invention is utilized for a making an additional incision.

By way of example, FIGS. 1–2 illustrate a direct-vision guide or dissector 5 in accordance with the present invention. FIG. 1 depicts dissector 5 with guide member 10 having proximal (near) and distal (far) ends, respectively 11 and 12, in an elongate generally cylindrical shape and fabricated from a transparent medical grade plastic. The overall length of guide member 10 for a nerve division procedure is approximately 250 mm., but such length may range from 150 mm. to 400 mm. for different procedures and is not limiting. Internal endoscope bore or scope lumen (cavity) 14 within guide member 10 extends from open proximal end 11 to closed distal end 12 to accommodate axial insertion of endoscope 22. Endoscope 22 for a nerve division procedure has a handle 23 and eyepiece 24 with a housing 25 having a diameter ranging from 5 to 10 mm. FIG. 3 illustrates a transverse sectional view of endoscope housing 25 having a bundle of optical fibers serving as a light guide (LG) and other optical fibers serving as an image guide (IG) with an objective lens 32 (FIG. 1) at the distal end 30 of the IG. It should be appreciated that guide member 10 may be dimensioned for any diameter endoscope ranging e.g. from 1 to 10 mm., either rigid or flexible, and be within the scope of the present invention and is described hereafter for use with an Olympus® model BF type 30 with 5.8 mm. diameter. The outside diameter of guide member 10 is approximately 11 mm. but may be any suitable diameter.

Longitudinally-extending working channel 34 may be any suitable diameter e.g. from 0.6 mm. to 5 mm. or more to accommodate accessory instruments. Working channel 34 is shown in FIGS. 1–2 being approximately 5 mm. diameter. Channel 34 has proximal and distal terminations, respectively 35 and 36. A conventional unitary duckbill silicon seal 38 is disposed in the proximal termination 35 of channel 34 to create a fluid-tight seal.

The distal end 30 of endoscope 22 abuts circumferential transition 48 between lumen 14 and reduced diameter lumen 40 to provide air space 49 between lens 32 and the inner face 53 of window 50. Air space 49 provides an adequate depth of field for the surgeon to view tissue pressed against or beyond window 50. Specialty endoscopes may be manufactured with a different angle distal end 30 in which lens faces, for example, from 90° to 45° relative to axis 55. As shown in FIG. 1, Olympus® model BF type 30 endoscope 22 has a 90° lens relative to axis 55 and provides an angle of view 56, for example, of 120° with a depth of field from 3.0 mm. to 50 mm.

Outer face 57 of transparent window 50 has a gently curved planar face or a generally flat planar face with a generally constant window thickness between inner face 53 and outer face 57. The outer face 57 is angled with respect to axis 55 at a suitable angle, for example between 20° and 60°, for reasons described hereinbelow. The periphery 58 of planar window 50 is generally elliptical with a rounded or dull edge resulting in a distalmost termination or tip 59 that is blunt and not capable of incising tissue.

The proximal end 11 of guide member 10 is coupled to handle 60. The proximal end 62 of plastic handle 60 is configured with a compression seal to secure endoscope 22 in guide member 10. Referring to FIG. 1, compressible washer 64 made of rubber or other suitable material is disposed in annular groove 65 in the proximal end 66 of scope lumen 14. Longitudinal slots 67 in handle 60 allow sleeve portions 68 to be displaced inwardly toward axis 55 to compress washer 64 against scope housing 25 when sliding plastic collar 69 is moved in the proximal direction. Indicator 70 is aligned with mark 72 on scope housing 25 to maintain the assembly in angular registration.

Referring to FIGS. 4–7, inflatable balloon 120 having interior inflation chamber 122 is disposed about the distal end 112 of guide member 10 and is made of a transparent non-elastomeric plastic sheet 123 such as PET-E®. The sheet 123 is formed into a balloon that when inflated is shaped like a "hot dog bun" (a rounded shape mostly but not completely surrounding a cylinder) with a central longitudinal "hot dog" shaped (cylindrical) lumen 124 that is not within inflation chamber 122. In transverse sectional view, the inflation chamber 122 has the appearance of a torus. Heat seals 125 bond together longitudinal edges 126a and 126b of sheet 123 to form cylindrical outer wall or sleeve 127. The balloon wall surrounding lumen 124 is similarly made of plastic sheet material to form inner wall or sleeve 128 with balloon proximal and distal ends, 129 and 131, heat sealed to enclose inflation chamber 122. The outer diameter of balloon 120 for spinal nerve division is approximately one and one-half inches but it should be appreciated that balloon 120 could be any suitable diameter or shape having a cylindrical shaped lumen for other procedures and be with in the scope of the present invention. Metal band 132 is press fitted over balloon 120 onto guide member 10 along with adhesives to make balloon chamber 122 fluid-tight.

Balloon constraining sleeve 133 is formed out of plastic sheet portion 134 and is employed to constrain balloon 120 in a first collapsed (uninflated) position around guide member 10. The constraining sleeve 133 is provided with a weakened plane consisting of perforations 135 which will give way and burst when an inflation medium is introduced into balloon chamber 122 allowing the balloon to deploy to the inflated (second) position.

As can be seen on FIG. 7, the distal end 12 of guide member 10 is not disposed within balloon inflation chamber 122 but within lumen 124. Balloon inner and outer walls or sleeves, 127 and 128, are shown in not-to-scale sectional illustration as folded inwardly in the longitudinal direction within each portion of the donut-shaped inflation chamber as shown in FIG. 7. The longitudinal inward fold may be singular or there may be a plurality of longitudinal inward folds, for example, to fit a more elongate balloon into a short constraining sleeve 133. FIG. 7 is a not-to-scale sectional illustration that depicts in the radial direction with respect to axis 55, outer balloon wall or sleeve 127 generally is folded radially inward in several portions and then overlapped or generally crushed inwardly toward axis 55 in order to be disposed with sleeve 133. As balloon 120 is inflated, it expands radially outwardly to unfold as well as deploying longitudinally by unfolding in the distal direction beyond the distal end 12 of guide member 10.

It should be appreciated that balloon 120 may be made of a substantially transparent elastomeric material such as latex and take on the elongated "hot dog bun" shape in the inflated or second position. In the collapsed (first) position, such a latex balloon is rolled inwardly in the longitudinal direction generally as depicted in FIG. 7 with the elastomeric characteristics of such a balloon radially collapsing the balloon walls onto guide member 10. A balloon constraining sleeve 133 to constrain an elastomeric balloon is made of nonelastomeric material as described above.

Inflation is provided for inflating balloon 120 by an inflation medium, preferably saline solution or carbon dioxide gas, by means of Luer-type fitting 137 at the proximal end 140 of inflation tube 142 which is connected to an inflation source, for example a syringe with saline solution (not shown). Inflation tube 142 is fixed to balloon 120 with an adhesive to communicate with inflation chamber 122 within balloon 120.

FIG. 8 depicts hold-down device 150 made of clear plastic having handle portion 151 and aperture 152 dimensioned to accommodate the projection therethrough of guide member 10.

FIGS. 9–10 depict flexible trocar 160 having flexible shaft 162 with a diameter that slidably cooperates with the bore diameter of working channel 34. The tip member 165 is made of a suitable material such as stainless steel and has three faces 167 with sharp edges 169 and sharp tip 170. The distal end 171 of flexible shaft 162 may be formed in a curve (see FIG. 9) in its repose position or it may be straight (see FIG. 10). Tip member 170 is fixed to shaft 162 with adhesives. The proximal end 172 of shaft 162 is coupled to handle 175.

Operation of the surgical instrument or dissector 5 shown in FIG. 1 may now be briefly described as follows. Endoscope 22 is inserted in scope lumen 20 until its distal end abuts transition 48. The surgeon slides collar 69 proximally which compresses washer 64 and secures endoscope 22 within member guide member 10.

Referring to FIGS. 11A–11H, assume that the surgical objective is the division of at least one dorsal ramus nerve exiting above or below the fifth thoracic vertebrae 178 to alleviate pain in region 179 on the patient's right side. The patient is prepared with a suitable anesthesia and the surgeon makes a small incision 180 along the midline of the patient's back about 2 to 4 vertebrae below the fifth thoracic vertebrae (see FIG. 11A). The surgeon inserts the distal tip 59 of guide member 10 into incision 180 and inwardly along the spinous process 181 and underneath overlying muscle 185 (FIG. 11F). The surgeon then advances blunt tip 59 more or less upwardly in the channel between the spinous process 181 and the transverse process 183 to a location about 2 to 4 vertebrae above the fifth thoracic vertebrae (see FIG. 11B). While thus advancing guide member 10, the surgeon views the progress of tip 59 through endoscope 22. As the surgeon applies axial pressure on guide member 10, the inclined face of window member 50 with respect to axis 55 in conjunction with blunt distalmost tip 59 will tend to follow the line of least resistance which is along a plane between overlapping muscle tissue 185 (see FIG. 11F).

If at times, endoscopic vision through window 50 becomes blocked or blurred by blood or secretions, the surgeon may move tip 59 from side to side or rotate the tip to wipe clean window 50. When the surgeon fiberoptically views landmarks such as a spinous process 181 in the desired location, he stops advancing the guide member 10. The surgeon also may locate distal end 12 of guide member 10 by the emission of light from the LG which results in a spot of light emitted through the translucent tissue overlying distal end 12 of the guide.

The surgeon easily may fiberoptically view anatomic landmarks and tissue through window 50 and he then identifies a region without nerves or blood vessels that is suitable for an additional or "inside-out" incision. He introduces trocar shaft 162 through working channel 34 until tip 170 is within his field of vision 56 beyond guide tip 59 and maneuvers trocar tip 170 to the site selected for the additional incision. While viewing through the endoscope, the surgeon or his assistant places hold down device 150 over the location of trocar tip 170 (see FIG. 11B) and presses downward while at the same time aligning tip 170 with aperture 152 in the hold down device 150. The surgeon's assistant may stabilize dissector 5 and the surgeon grasps trocar handle 175 and advances trocar tip 170 in the distal direction and outwardly until trocar tip 170 projects through the tissue and skin overlying the dissected anatomic space thus making an "inside-out" incision 188 from the interior of the body to the exterior of the body (see FIG. 11D). During the advancement of tip 170 of trocar 160, the surgeon may find it useful to rotate handle 175 of the trocar to facilitate making the incision.

After trocar tip 170 is projected outwardly from the skin, a standard 5 mm. diameter cannula assembly 190 is placed over trocar tip 170 and trocar shaft 162. Using the trocar shaft as a guide, the surgeon can telescopically advance cannula 192 inwardly into additional incision 188 until distal end 194 of the cannula is disposed within the dissected space in the interior of the body (see FIG. 11D). Thereafter, trocar 160 is withdrawn from working channel 34 and set aside. As an alternative, it should be appreciated that guide member 10 could be advanced in the distal direction over shaft 162 of "inside-out trocar" 160 and the tapered tip 59 of guide member 10 can easily be pushed through tissue to be exposed outside the body, again using hold-down device 150 as described above. This manner of using the invention would allow for easy insertion of a larger diameter 11–12 mm. cannula over guide member 10 and into incision 180 in order to accommodate a larger diameter accessory instrument. As a next option, an external source of carbon dioxide insufflation may be connected to cannula assembly 190 to insufflate the dissected space within the interior of the body. Such insufflation pressure could assist in dissecting tissue in space 177 along with inflation balloon 120 (see FIG. 11H).

Thereafter, the surgeon withdraws guide member 10 slightly in the proximal direction away from distal end 194 of the cannula and begins to inflate balloon 120 with an inflation medium such as saline solution from a syringe 195 (see FIG. 11E). The saline solution has an index of refraction similar to that of the plastic balloon wall and provides for better fiberoptic viewing therethrough when compared with carbon dioxide. Slight expansion of balloon 120 causes constraining sleeve 133 to burst along the perforations 135 thus permitting the balloon to deploy and inflate to its second position. After balloon 120 is disposed in its inflated (second) position, the radius of the balloon's outer cylindrical shape provides an increased depth of field in all directions around lens 32 of endoscope 22.

With the balloon in the inflated position, the surgeon easily may view anatomic landmarks and structures through the transparent balloon walls. The surgeon may move guide member 10 axially within balloon lumen 124 which generally will cause the exterior wall 127 and interior wall 128 of the balloon to "roll" along guide member 10 since the balloon is secured to guide member 10 at one point only by metal band 132. As balloon 120 thus rolls over guide member 10, the exterior wall 128 will be maintained in a fixed position against surrounding tissue due to inflation pressure. To facilitate such reciprocation of guide member 10 within lumen 124, the surgeon's assistant may deflate and inflate the balloon slightly as necessary to maintain the balloon in the second position. The axial movement of guide member 10 allows the surgeon to view certain structures such as dorsal ramus nerve 199 outside the exterior balloon sleeve 127. Such nerves are less stretchable than surrounding soft tissue and should cause balloon wall 127 to "tent" substantially inwardly into balloon chamber 122. FIG. 11F and 11G illustrate a sectional view of guide member 10 introduced along vertebrae 178. FIG. 11H is a partial longitudinal sectional view of balloon 120 in an inflated or second position.

To complete the division of dorsal ramus nerve 199, the surgeon introduces scissors 202 (see FIG. 11E) through cannula assembly 190 into the interface between the exterior of balloon wall 127 and the surrounding muscle 186 (see FIG. 11H). The surgeon then advances scissors 202 along the exterior surface of balloon 120 while viewing through endoscope 22 from the inside of the balloon lumen 124. By moving the scissors 202 back and forth and around balloon 120, the surgeon can maneuver the cutting blade of scissors 202 into position, open the jaws of the scissors and then divide nerve 199.

Although the present invention has been described in conjunction with a division of a nerve, it should be appreciated that the instrument and method of the present invention can be utilized in other surgical procedures. More in particular, the same techniques can be used to make additional "inside-out" incisions safely in abdominal endoscopic procedures to avoid making inwardly-directed additional incisions with puncturing trocars. In co-pending application Ser. No. 08/187,753 dated Jan. 26, 1994 now abandoned (incorporated by reference herein) there is disclosed a device and method for safely making a first incision with a heliscopic cutting device into the abdominal cavity and for placing a cannula into the abdominal cavity to allow for insufflation of the cavity. It has been found that it is often difficult to make additional incisions into an already insufflated abdominal cavity without at times causing undesired injuries to sensitive structures within the abdominal wall, such as a blood vessel, an artery or a nerve.

For example, operation of instrument 5 for making an additional "inside-out" incision in an already insufflated abdominal space may be described briefly as follows. Referring to FIGS. 12A–12D, a heliscopic cutter or another commercially available trocar is utilized to place a standard 10–12 mm. diameter cannula assembly through the abdominal wall in incision 211 allowing for insufflation of the abdominal cavity (see FIG. 12A). Guide member 10 of the present invention then can be inserted through cannula assembly 212 as shown in FIG. 12B and the surgeon can view sensitive structures on the inside of the abdominal wall from within the insufflated abdominal cavity through endoscope 22. The surgeon then can select a safe location for an "inside-out" incision and use the aforementioned procedures to advance 5 mm. diameter trocar tip 170 through the abdominal wall with the use of hold down device 160 to make incision 228 (see FIG. 12C). Thereafter, the surgeon advances a standard 5 mm. cannula 132 over the exposed trocar tip 170 and into the "inside-out" incision 138 (see FIG. 12D).

A second embodiment of an instrument 235 is more specifically adapted for making "inside-out" incisions for example in an abdominal cavity and is illustrated in FIGS. 13–14 with endoscope 22 disposed therein. Guide member 240 is made of transparent medical grade plastic and differs from the earlier described embodiment in that the guide has no working channel or balloon member. Distal end 242 of guide 240 has a closed end with window 250 and terminates in a substantially sharp tip 245 and a sharp distal window edge 246 that generally are capable of incising tissue.

Operation and use of guide 240 shown in FIGS. 13–14 is briefly described as follows. Assume that an abdominal endoscopic procedure is to be performed that requires three cannula assemblies for an endoscope and two accessory instruments. Cannula 212 already has been placed into the abdominal cavity in the patient at incision 211 near the umbilicus as shown in FIG. 15A. The surgeon then introduces guide member 240 of instrument 235 through cannula 212 into the abdominal cavity. As distal end 242 of guide member navigates within the abdominal cavity, the surgeon views through endoscope 22 the inside of the abdominal wall and sensitive anatomic structures in the inner face of the wall. The surgeon then directs the substantially sharp tip 245 of guide member 240 to a safe location for an additional incision. The surgeon or his assistant places hold down device 150 in position as previously described. As the surgeon begins to push tip 245 outwardly into the tissue of the abdominal, the lens 32 of endoscope 22 is very close to the "inside-out" incision and moves with tip 245 thus affording excellent viewing of the exact tissue area being incised. The instrument also may be rotated to closely view all tissue in the incision area. Such close visualization is somewhat improved over the previously described embodiment in which lens 32 may be held stationary while the inside-out trocar is advanced. FIGS. 15C–15D shows tip 245 exposed outside the patient's skin after making additional incision 248.

FIG. 15D illustrates second cannula assembly 252 with cannula 254 being prepared for insertion into incision 248 using tip 245 as a guide. The bore in cannula 254 is dimensioned to fit closely over the cylindrical shape of guide member 240 to allow easy insertion into incision 248. FIG. 15E illustrates additional incision 258 made for a third cannula (not shown).

It should be appreciated that tip 245 of guide member 240 does not need to be razor sharp to easily make an inside-out incision. As the surgeon begin to advance tip 245 outwardly and the patient's skin tents outwardly, the surgeon may cut inward with a scalpel to meet tip 245 and thereafter advance the tip outwardly from the skin.

A third embodiment or instrument 335, very similar to the last described embodiment, is depicted in FIGS. 16–17 with guide member 340 having proximal and distal ends, 341 and 342. This guide differs from the previous embodiment only in that it has an open distal end 342 and is made of a thin walled metal or plastic tubular member. Guide member 340 terminates in a sharp tip 345 with a blade-like edge 346 that is capable of incising tissue. Guide 335 is used in the manner shown in FIGS. 15A–15E.

Although the present invention for dissecting a fiberoptic viewing space in the interior of the body and the manner of performing a procedure on the surface of an inflated balloon has been described principally in conjunction with the division of a nerve, it should be appreciated that the device and method hereinbefore described can be used for other surgical procedures. For example, the instrument and method can be used for any procedure in which it is useful to dissect a "minimally invasive" accessway along an anatomic plane to a remote region for performing a procedure such as the dissection of a lymph nodes, the excision of a cyst, or for biopsy sampling.

I claim:

1. A method for making at least one outward incision in a body for cannula placement using an elongate guide member, comprising the steps of:
    introducing a distal extremity of the guide member through a first incision into the interior of the body at a first region;
    advancing the distal extremity of the guide member within the interior of the body to a second region remote from the first region; and
    advancing the distal extremity of the guide member outwardly from the interior of the body in the second region until the distal end of the guide member projects outwardly from the skin of the body, thereby making the at least one outward incision in the second region.

2. The method of claim 1, further comprising the step of holding down the skin in the second region with a hold down device to permit the distal extremity of the guide member to advance outwardly from the skin through the hold down device.

3. The method of claim 1, further comprising the step of placing a cannula over the distal end of the guide member that projects outwardly from the skin in the second region and advancing the cannula inwardly toward the interior of the body over the guide member until the distal end of the cannula is disposed within the additional incision.

4. The method of claim 3, further comprising the step of withdrawing the distal end of the guide member from the cannula that is disposed within the additional incision.

5. The method of claim 3, wherein said advancing to a second region includes advancing the distal extremity between overlapping muscle tissue.

6. The method of claim 1, further comprising the step of viewing through the guide member the advancement of the guide member in the interior of the body from the first region to the second region.

7. The method of claim 1, further comprising the step of creating an anatomic space between the first region and second region by blunt dissection of tissue between the first region and second region.

8. The method of claim 7, further comprising the step of insufflating the space that was bluntly dissected between the first region and second region.

9. The method of claim 1, further comprising making said first incision in a first region of the body prior to said introducing step.

10. The method of claim 9, wherein the first incision making step comprises penetrating the distal end of the guide member through the skin into the interior of the body.

\* \* \* \* \*